United States Patent [19]
Goldowsky

[11] 3,931,818
[45] Jan. 13, 1976

[54] LIQUID ADMINISTRATION APPARATUS

[76] Inventor: Michael Goldowsky, 222 Marthling Ave., Tarrytown, N.Y. 10591

[22] Filed: July 22, 1974

[21] Appl. No.: 490,777

[52] U.S. Cl. ............... 128/214 C; 128/227; 222/55; 222/67
[51] Int. Cl.² .......................................... A61M 5/14
[58] Field of Search ........ 128/214 R, 214 C, 214 E, 128/214.2, 227; 222/55, 67–69

[56] References Cited
UNITED STATES PATENTS

| | | | |
|---|---|---|---|
| 1,844,342 | 2/1932 | Berman | 215/100 |
| 2,090,273 | 8/1937 | Wagner | 128/214 C X |
| 2,865,534 | 12/1958 | Barnes | 222/68 X |
| 3,001,397 | 9/1961 | Leonard | 128/214 C X |
| 3,216,418 | 11/1965 | Scislowicz | 128/214 C |
| 3,756,233 | 9/1973 | Goldowsky | 128/214 C |

FOREIGN PATENTS OR APPLICATIONS

| | | | |
|---|---|---|---|
| 1,197,910 | 7/1967 | United Kingdom | 128/214 C |

OTHER PUBLICATIONS
Lancet — Apr. 6, 1963 — pp. 754–755.

*Primary Examiner*—Dalton L. Truluck
*Attorney, Agent, or Firm*—Stanley J. Yavner

[57] ABSTRACT

A liquid administration apparatus includes a closed fluid system enabled by a double bore metering tube which leads from an intermediate sump fed by a supply container to a flow controlling float chamber. The supply container can either be of the flexible bag type or the bottle type, both commonly used for infusing physiological fluids into the circulatory system of a patient. The float chamber is movably mounted on a flow indicating scale to set calibrated rates of flow. The sump is divided into a reservoir portion and an over-flow portion by a dam and an air inlet tube projects above the dam. A liquid inlet means leads from the reservoir portion through a metering tube to the float chamber. The float chamber includes a float which is buoyed by liquid entering the float chamber and centered by splines projecting inwardly of the float chamber. The float in the float chamber functions as a valve to selectively open and close a port leading to the infusion needle of the apparatus. In one alternative embodiment the float chamber is made transparent since drops of physiological fluid are formed in that chamber. In the preferred embodiment, drops are formed only in the sump and the sump is therefore made transparent for observation of the functioning of the apparatus. Specifically, a closed system is presented whereby a pressure equalizing air tube connects the sump and the float chamber, neither of which is vented to the outside atmosphere. This makes the system self-compensating in maintaining a constant head for the fluid between the sump and the float chamber.

11 Claims, 11 Drawing Figures

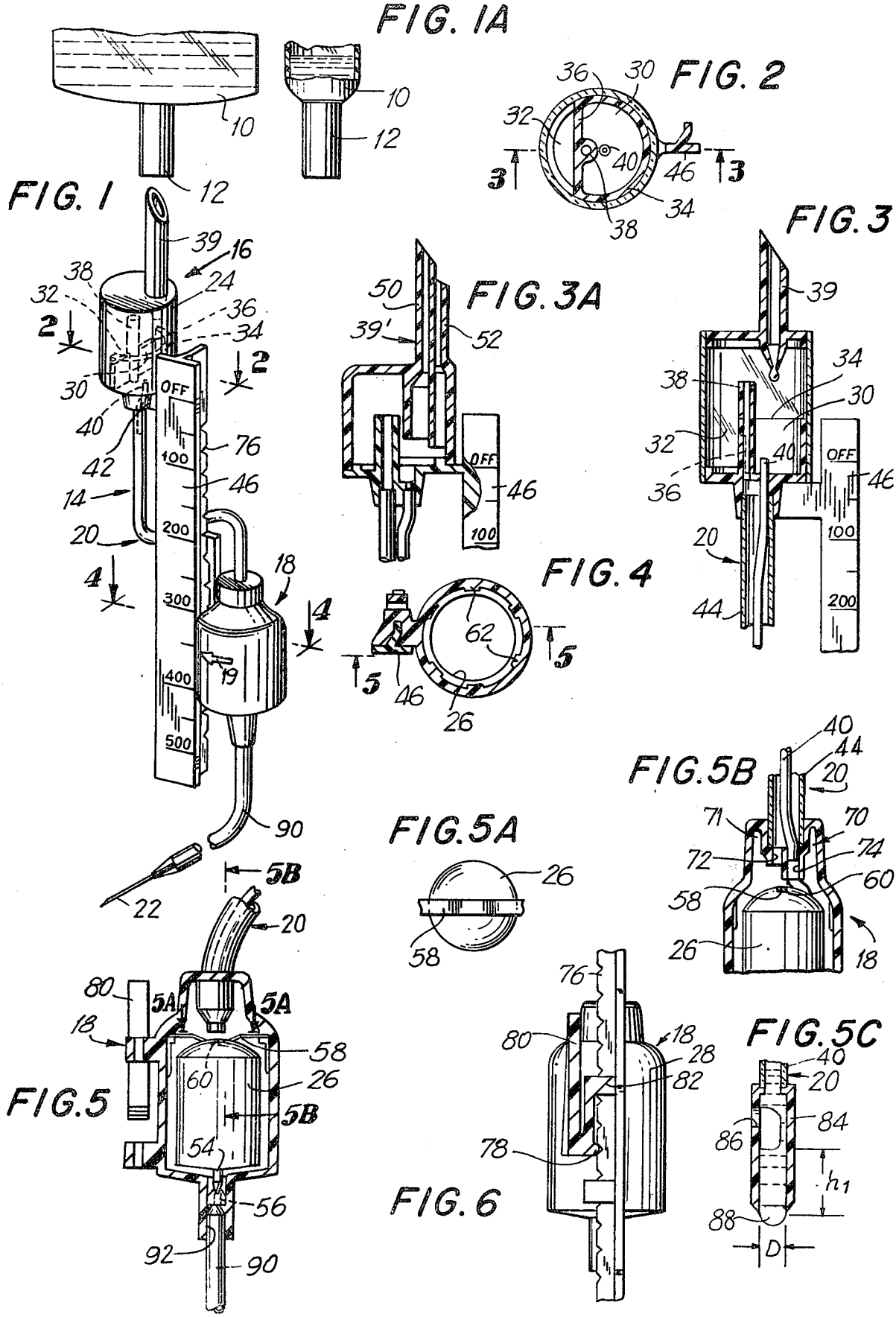

LIQUID ADMINISTRATION APPARATUS

This invention relates primarily to liquid administration apparatus and more particularly to such apparatus wherein flow rate is maintained at a constant value without regard to the amount of liquid remaining in the supply container.

Physiological fluids are normally infused into a patient with a parenteral administration set. The administration set is utilized to provide a fluid passage between a physiological fluid in a supply container, e.g., a parenteral solution of sterile water or a saline or glucose water solution, etc., carried in a glass bottle or in a flexible plastic bag for intravenous or arterial administration. Infusion of the parenteral solution has been achieved by suspending an inverted bag above the patient and interconnecting a length of tubing forming a part of the administration set to the bag by piercing a membrane stopper at the mouth of the bag with a penetrant. The tubing included a drip chamber connected in series therewith and through which the rate of solution flow could be observed. A constriction pinch valve was provided to restrict the fluid flow through the tubing to levels meeting the prescribed requirements of the patient. The free end of the tube was connected to a hollow bore needle which was inserted into a blood vessel, e.g., a vein, of the patient.

When the supply container was a vented bottle or a collapsable bag, it suffered from the disadvantage that the flow rate changed as the bottle emptied and the fluid head reduced.

A major disadvantage encountered with either supply container, rigid, vented bottle or collapsable plastic bag, is the variation that took place relative to rate of solution flow. The flow rate changes could be compensated for by a technician observing the drip rate and accordingly adjusting the aforementioned construction pinch valve. Furthermore, flow rate changes could be caused not only by depletion of the liquid supply in the supply container, but also when the patient voluntarily or involuntarily raised or lowered his infusion arm. Also, changes in blood pressure, partial clogging of the infusion needle or partial clogging at another part of the administration set could cause changes in the flow rate. Although recent advances have been made relative to elimination of particulate matter infused into the patient by the use of filters at the infusion needle, clogging can still occur without use of the present invention at the constriction pinch valve, which clogging is not alleviated by an infusion needle filter.

The constant and gradual changes in flow rate necessitated the constant checking and adjustment of administration sets by overburdened nurses. Furthermore, flow rate stability has been insufficient for pediatric and cardiac patients where expensive infusion devices must be used.

Accordingly, a primary object of the present invention is to provide a liquid administration apparatus for providing constant flow without regard to the level of the infusion arm, clogging problems, the amount of fluid remaining in the supply container or the patient's blood pressure.

A further object of the present invention is to provide liquid administration apparatus which can be used with a flexible plastic bag liquid supply container or a vented, rigid supply container.

These and other objects of the present invention are accomplished in accordance with one illustrative embodiment of the present invention which features an administration set for the infusion of a supply liquid in a supply container into the circulatory system of a patient. The administration set includes a sump and a float chamber connected by a double bore metering tube for carrying air and liquid between the sump and the float chamber. The supply container can either be of the flexible bag type or the rigid, bottle type, both commonly used for storing physiological fluids. The float chamber is movably mounted on a flow indicating scale and includes a float which is buoyed by liquid entering the float chamber from the sump. Projecting inwardly from the float chamber shell are splines for the purpose of centering the float, which acts as a normally closed valve relative to liquid flowing from the float chamber through the infusion needle of the apparatus. In one embodiment the float chamber is made transparent since drops of the liquid are formed in that chamber, but in the preferred embodiment, drops are formed in the sump and the sump is made transparent for observation of drop formation.

The sump is divided into a reservoir portion and an over-flow portion by a dam construction, with the reservoir portion supplying the liquid bore of the metering tube, and an air inlet tube projects above the dam construction.

In one alternative embodiment a vented nozzle leads from the metering tube to the float chamber whereby drops are made to form in the float chamber.

The above brief description, as well as further objects, features and advantages of the present invention, will be more fully appreciated by reference to the following, detailed description of the preferred, but nonetheless illustrative embodiment, when taken in conjunction with the accompanying drawings, wherein:

FIG. 1 is a front perspective view of an administration set apparatus according to the present invention, showing particularly the physiological fluid bag and the infusion needle with which said administration set is connected for operation;

FIG. 1A is a side, partially sectioned view of the physiological fluid bag;

FIG. 2 is a top sectional view of the sump apparatus of the administration set, the section being taken along line 2—2 of FIG. 1;

FIG. 3 is a front, partial section view taken along the line 3—3 of FIG. 2 and showing particularly the dam construction dividing the portions of the sump;

FIG. 3A is a front, partial, sectional view of an alternative sump inlet means useful in the system of FIG. 1;

FIG. 4 is a top, sectional view of the float chamber of the administration set, taken along the line 4—4 of FIG. 1;

FIG. 5 is a front, sectional view of the float chamber with float therein taken along the line 5—5 of FIG. 4;

FIG. 5A is a partial top view taken along the line 5A—5A of FIG. 5;

FIG. 5B is a front, partial, sectional view of the float chamber inlet means taken along the line 5B—5B of FIG. 5;

FIG. 5C is a front, sectional view of an alternative inlet means useful in connection with the float chamber of FIGS. 5 and 5B when the sump of FIG. 3A is used; and FIG. 6 is a partial side view showing the float chamber and scale of FIG. 1 and particularly the construction for moving the float chamber with a ratchet and pawl type mechanism.

Referring to the drawings, a liquid administration apparatus is shown for use with either a rigid fluid bottle (not shown) or a collapsable, plastic, physiological fluid bag 10. Depending from the fluid bag 10 is a flexible neck 12 for attachment of the fluid bag to the administration set generally designated 14, of the present invention.

The administration set 14 is generally divided into three main portions: a sump apparatus, generally designated 16, a float chamber generally designated 18 and a metering tube generally designated 20.

The metering tube is primarily for the purpose of providing a fluid conduit from the sump apparatus to the float chamber, the sump apparatus 16 providing an intermediate fluid storage capability and the float chamber 18 providing a valve capability for the administration set 14. The fluid is conducted in a controlled flow from the float chamber to infusion needle 22 commonly found in most administration sets. Infusion needle 22 is connected to infusion tube 90 which fits into opening 92 defined by the lower surface of float chamber 18.

Referring particularly to FIGS. 1 and 1A, the flexible, physiological fluid bag 10 is preferred for use with the administration set 14 of the present invention primarily since contaminating outside air does not enter the system as it does in vented bottles. Sump level variation in the administration apparatus using the administration set 14 of the present invention is purely a function of the relative sizes of sump container 24 of the sump apparatus (e.g. 1 inch D), the diameter of float 26 (e.g. ¾ inch D) of float chamber 18 (see FIG. 5), flow clearance between float 26 and shell 28 (e.g. 1/64 inch) of the float chamber (see FIG. 5), and other fixed physical properties of the administration apparatus, which can be designed so that sump level variation and flow rate changes are minimal as the bag or bottle empties.

Furthermore, shaking or squeezing of the bag 10 has a minimal effect on system performance since the administration set of the present invention is designed as a closed system (without venting) which automatically self-compensates, stabilizing the fluid level.

Of course, as an alternative supply, a tube type vented bottle can be used with an administration set 14 according to the present invention. The ambient vented air displaces the supply fluid in the supply container just as does the collapsing flexible bag recommended for use with the present invention.

Sump apparatus 16 is constructed to include a flexible plastic sump container 24, which has therewithin a reservoir portion 30 and an over-flow portion 32 (see FIGS. 1, 2 and 3). Reservoir portion 30 is defined by a semicircular wall 34 and is separated from over-flow portion 32 by a dam wall 36. Dam wall 36 includes a central, circular air inlet tube 38 which extends upwardly from the bottom wall of sump container 24 by an amount greater than the upstanding extent of semicircular wall 34, which in turn extends upwardly by a greater extent than dam wall 36.

Sump inlet tube 39 is constructed to function preferably as a drip nozzle to supply fluid from fluid bag 10 to reservoir portion 30. Furthermore, liquid inlet tube 40 provides an exit for the fluid from sump apparatus 16 to metering tube 20. Thus, liquid inlet tube 40 (approx. 1/32 inch D) either extends beside air tube 44 to form the metering tube 20 or it extends within air tube 44 for purposes of providing more compact construction.

Accordingly, sump apparatus 16 functions by the operator squeezing flexible sump container 24 to force air into fluid bag 10 by means of sump inlet tube 39 being placed within flexible neck 12. The air thus forced into fluid bag 10 causes fluid to flow down through sump inlet tube 39 into reservoir portion 30 of sump apparatus 16. The height of dam wall 36 fixes the level of fluid in reservoir portion 30 with any excess fluid overflowing into over-flow portion 32. All or part of sump container 24 is made transparent so that dripping from sump inlet tube 39 into reservoir portion 30 is readily observable by the operator.

In an alternative embodiment, sump inlet tube 39, shown in FIG. 3, is located in the sump with a downward extent great enough so that the fluid from fluid bag 10 rises to the lowermost level of tube 39 when the flexible sump is squeezed. In this way, when the sump level becomes well defined (reaching tube 39 by the expelling of air), no drops are formed and observation of dripping is provided instead by the use of a nozzle in a transparent float shell. In this alternative embodiment, air inlet tube 38 is located above the fluid level.

Sump apparatus 16 also includes a bottom cap 42 through which metering tube 20 leads, bottom cap 42 being molded integrally with scale 46. A web may be extended from the metering tube sockets to stiffen and support the scale.

In another alternative embodiment shown in FIG. 3A, a self-filling sump includes a penetrant 39' having two ports 50,52. The advantage of this embodiment is that the sump level automatically stabilizes at the bottom of air port 50 when the bag is initially inverted. It is therefore not necessary to squeeze the sump, as in the preferred embodiment, and the sump may therefore be constructed entirely of either flexible or rigid material. More specifically, FIG. 3A shows sump inlet tube 39' including air port 50 and fluid port 52 for extending into the flexible neck 12 of the fluid bag 10. This alternative embodiment has the advantage that the sump is self-filling and need not be squeezed. Fluid port 52 is located substantially below the small diameter air port 50. The pressure differential formed when initially inverting the bag causes fluid to go down fluid port 52 and further causes sump air to rise into the bag via air port 50. When the fluid level rises to the lowermost extent of air port 50, it stops at the well-defined location, which is substantially the same level as the level determined by dam wall 36 in the preferred embodiment of FIG. 3. The diameter of sump inlet tube 39' at its lowermost extent is sufficiently enlarged over the lesser diameter of the upper part of sump inlet tube 39' so that initial flow separates at the tapered junction and the lowermost part of sump inlet tube 39' does not fill with fluid. Air then can freely pass up through air port 50 due to the buoyancy thus achieved. The sump container in this embodiment may be made of rigid plastic, which need not be transparent since drops are formed only in a transparent float chamber using a nozzle such as that shown and to be described with reference to FIG. 5C. When the alternative embodiment of FIG. 3A is used, a transparent float chamber 18 having transparent shell 28 would provide an observation capability for the operator of the administration apparatus. It may be seen from FIG. 3A that no drip space is provided between the bottom of sump inlet tube 39' to the expected fluid level in the sump.

As is shown most clearly in FIG. 3, the preferable construction of metering tube 20 is such that liquid inlet tube 40 is located within and generally concentric to air tube 44. Metering tube 20 leads from sump apparatus 16 to float chamber 18 terminating at a point within shell enclosure 28 of the float chamber. Within float chamber 18 is a thin-walled float 26 depending from which is float valve stem 54. Shell 28 defines at its lowermost point or supports at its lowermost point rubber valve seat opening 56 leading to infusion needle 22.

As shown in FIG. 5A, spring 58 is fixedly supported or positioned by float chamber shell 28 such that it downwardly biases float 26 to provide a normally closed valve system. Spring 58 contacts float 26 by resting on concavity 60 as defined by the top of float 26. Thus, when fluid flows from fluid bag 10 through reservoir portion 30 of sump apparatus 16 and then through liquid inlet tube 40 of metering tube 20 into float chamber 18, fluid collecting at the bottom of float chamber 18 causes float 26 to rise and thereby opens the valve system by removing valve stem 54 from valve opening 56. Of course, to provide such functioning, float 26 is constructed with thin walls and hollow construction as shown most clearly in FIG. 4.

Also shown in FIG. 4 are a plurality of splines 62 whose function it is to center float 26 within float chamber 18. Thus, the disadvantages of a tilting float 26 or an uneven distribution of fluid within float chamber 18 are avoided which would otherwise cause unbalanced surface tension forces impeding the motion of the float. Alternatively, a plurality of splines or tabs can extend outwardly around the periphery of float 26 to provide the centering function without the necessity for inwardly directed splines extending from float chamber shell 28.

Float chamber inlet means, generally designated 70, is shown in FIG. 5B wherein float chamber air inlet port 72 is adjacent float chamber fluid inlet port 74, the latter of which extends into float chamber 18 to a greater extent than does the former. Fluid entering float chamber fluid inlet port 74 is accordingly not provided, as shown in FIG. 5B, with sufficient drip space relative to float 26. On the other hand, fluid coalesces directly with float 26 from float chamber fluid inlet port 74 and flows down the sides of float 26 to the bottom of float chamber 18. This eliminates back pressure variations associated with forming drops. Consequently small heads of fluid may be used with reliable operation, thus providing the administration set with a very large flow rate range typically in excess of forty to one.

Float chamber 18 is movably connected by means of a T-slide to scale 46 as shown in FIG. 4. Of course, a dovetail cross-sectional construction mating float chamber 18 with scale 46 would also function properly, but the preferred design shown in FIGS. 4, 5 and 6 is much easier to mold and requires less plastic. Ratchet teeth means 76 are provided along the scale for selective engagement with a pawl 78 extending from lever 80. Bearings 82 are integrally molded with float chamber 18 and lever 80 so that when lever 80 is depressed (FIG. 6), pawl 78 lifts from a ratchet slot (defined by teeth means 76), and float chamber 18 can be raised or lowered to any other ratchet slot position. Downward pulling on float chamber shell 28 tends to tighten the engagement because of the moments of force involved. This makes downward slippage impossible.

A small button (not shown) is molded at the bottom of the scale to keep float chamber 18 from coming off the scale. A similar but smaller button (e.g., in the form of a flexible tab) (not shown) is used at the upper part of the scale (molded thereon) to enable the float chamber to be installed onto the scale, but not removed. With this arrangement and construction, the float chamber 18 is allowed complete freedom of vertical movement (but with a bottom and upper limit) in a smooth and efficient manner. A slot spacing of ⅛ inch gives a flow rate resolution of 2½ percent for a 5 inch long scale which is more than adequate for medical applications. Variations on the scale and motion design are contemplated and within the limits of the invention detailed herein.

As an alternative design for the float chamber inlet means, a vented nozzle 84 is shown in FIG. 5C in order to provide drop formation without significant drop formation pressure feedback. Vented nozzle 84 defines vent opening 86 such that fluid entering from metering tube 20 causes fluid to trickle down the inside of vented nozzle 84 to thereby isolate the level variation that is caused by the forming drops 88. In other words, the end of liquid inlet tube 40 of metering tube 20 only "sees" the air pressure in the float chamber 18. For the embodiment of FIG. 5C, the nozzle exit D is chosen for the desired drop size. The smaller D is, the larger $h_1$ will be (the maximum height of fluid before drop 88 falls). With a large $h_1$, the nozzle will be longer. Accordingly, with a drop size of 20 drops per cubic centimeter, length $h_1$ is on the order of ¼ inch, making for a compact design. With this alternative embodiment including a vented nozzle 84, no pressure variation can affect the metering tube.

In order to provide a more complete description of the present invention, a series of operational steps will now be described with reference to an administration set 14 according to the present invention.

Upon detecting the requirement for physiological fluid, the operator inserts pointed sump inlet tube 39 into flexible neck 12 of a flexible fluid bag 10, thus puncturing the membrane. With the lower end of sump inlet tube 39 functioning as a drip nozzle in a transparent sump container 24, the flow of the system is then begun by squeezing flexible sump container 24 which pushes air up through sump inlet tube 39 to the space above the fluid in flexible bag 10. Fluid then flows into reservoir portion 30 until the level of the top of dam wall 36 is exceeded, so that any over-flow goes into over-flow portion 32. An equilibrium of pressure is always present between float chamber 18 and the inside of sump container 24 by means of the connecting air tube 44. Shaking or squeezing of fluid bag 10 has minimal effect on fluid levels since it is a closed system. Any increase in air pressure as would momentarily occur when squeezing fluid bag 10 is equalized on each end of air tube 44, so that no flow rate change occurs. As soon as the fluid bag 10 is released after squeezing, the collapsing or lowering of the fluid in the bag allows the level of fluid in reservoir portion 30 to revert to its normal level.

Furthermore, if the patient raises his infusion arm above the sump apparatus, even to a point slightly below the fluid level in fluid bag 10, flow rate will remain constant because of the pressurized drip and float chambers provided by the sump apparatus as shown and air tube 44 of metering tube 20.

As fluid flows through liquid inlet tube 40 as supplied by fluid in reservoir portion 30, it coalesces with float 26 upon entering float chamber 18. It should be noticed at this point, in FIG. 5B, that float chamber fluid inlet port 74 extends lower than float chamber air inlet port 72 in order to keep the air tube or port from getting wet. In case the float chamber is inadvertently inverted or a new bag is installed, fluid in those cases would merely fill annulus space 71.

As fluid flows into float chamber 18, the clearance around float 26 begins to fill up at the same time as the fluid level within the much larger cross-sectional fluid area of sump container 24 is going down. If the valve system in float chamber 18 at this point were to remain closed, no fluid would come out of fluid bag 10, since the sump apparatus and float chamber form a closed system by means of air tube connection 44. However, as the float 26 attains buoyancy and lifts (opening the valve), fluid leaves the system through infusion tube 90. Because of the closed system, an equal amount of fluid as has left through infusion tube 90 comes out of fluid bag 10 and into reservoir portion 30 to replenish it. This process continues with the level of fluid in reservoir portion 30 remaining constant as fluid is infused. Any tendency of the level of fluid in reservoir portion 30 to go down will cause a partial vacuum in the air space above the fluid within sump container 24 creating a differential pressure across sump inlet tube 39, thus forcing fluid out of the bag and into reservoir portion 30. This same pressure differential forms drops on tube 39 without causing back pressure across tube 44. This theory of operation insures constant flow in the event of the infusion arm being lifted as previously described. Any lifting of the infusion arm will cause the fluid level to rise in float chamber 18, thus lifting the float slightly. This decreases the closed system's air volume, which in turn results in the sump level lowering slightly. However, with a large enough sump apparatus container 24 (in cross-sectional area) such a sump level change will be minimal and will be inconsequential to the accuracy of the infusion rate.

When an infusion arm is lowered, thus reducing the infusion back pressure, float 26 lowers, constricting the valve slightly, and the system's air volume tends to increase very slightly. Accordingly, the fluid level in reservoir portion 30 will rise very slightly, but a constant flow rate through liquid inlet tube 40 can be maintained indefinitely.

As the fluid level reduces in fluid bag 10, air pressure decreases in the sump and float chamber; but obviously, flow rate through the liquid inlet tube 40 remains the same by means of the pressure equalization function provided by air tube 44. The fluid level drops slightly on the order of a few thousandths of an inch within sump container 24, causing a decrease in system air pressure, which automatically matches the reduced head from the fluid bag with no effect on flow rate.

Any minor adjustments that are desired for changing flow rate are made by means of scale 46 providing on its face numerical indicia. The indicia are consecutively numbered and uniformly spaced to provide a flow adjustment capability in terms of cubic centimeters per hour, as an example. An indicator reference such as an arrow 19 positioned on the outside surface of float chamber 18 enables such adjustments. Thus, an effective head of the system can be varied by means of raising or lowering the float chamber, as is explained in U.S. Pat. No. 3,756,233, inventor — Michael Goldowsky, entitled Liquid Administration Apparatus, issued Sept. 4, 1973. Adjustment of the float chamber to cause an indicating arrow to point to the "off" line or above of scale 46 terminates flow in the system by bringing the float chamber fluid inlet port 74 to the same elevation as the fluid in the sump reservoir 30.

The flow rate accuracy of the scale reading is not in error for fluids of the viscosity chosen for its calibration. Since the percent glucose content of the intravenous fluid is the overwhelming constituent determining viscosity, a conventional intravenous set may be calibrated for use with 5 percent glucose solutions, the most often used solutions. For solutions containing no glucose, the rate of flow is a convenient 10 percent faster and likewise 10 percent slower for the 10 percent glucose solutions. These changes are easily compensated for, if desired, when setting the flow rate. In all cases, however, the rate of flow can always be determined, checked or altered by the conventional method of counting drip rate in the drip chamber.

With intravenous sets for special applications such as hyperalimentation, where 50 percent glucose may be used, the metering tube liquid bore is made slightly larger and the administration set precalibrated for the nominal 50 percent glucose solution.

The extruded accuracy of the metering tube bore is not critical because flow calibration of the device is only determined by the metering tube flow resistance, which in turn depends upon its length. On an individual tube to tube basis, a length of tube is first cut off a spool. An automatic machine then passes air through the tube at a fixed pressure differential and cuts the tube length until a set flow rate of air is observed. Thus, in a matter of seconds, flow rate calibration is effected to very high accuracy. For example, a 6 inch long metering tube need only be cut off within plus or minus 1/16 of an inch of its true length for plus or minus 1 percent flow rate accuracy of the scale.

What is claimed is:

1. An administration set for the infusion of a supply liquid in a supply container into a separate liquid system comprising means for forming an access for liquid flow from the container, sump means having an air space and for providing an intermediate reservoir and flow of liquid, float chamber means for controlling liquid flow from said sump means, metering flow means for providing a conduit for said liquid from said sump means to said float chamber means and moveable support means for said float chamber means for maintaining a substantially constant head of fluid between said sump means and said float chamber means, infusion tubing for conducting liquid from said float chamber means to said separate liquid system, said metering flow means including first and second fluid passages for simultaneous liquid and air flow respectively at an air pressure other than atmospheric to eliminate substantial pressure differentials between said sump means and said float chamber means during delivery of said liquid to said separate liquid system and said second fluid passage extending into said sump means in communication with said air space, whereby as said supply container empties, the flow rate through said metering flow means remains substantially constant.

2. The invention according to claim 1 wherein said float chamber means includes a float and a float chamber outer shell, a chamber defined by said float chamber outer shell for containing liquid to buoy said float, a float valve stem projecting downwardly from said float, said float chamber outer shell defining a valve seat opening constructed to receive said stem and one of said float chamber shell and float including a plurality of centering splines for centering said float, said centering splines being constructed and arranged to provide a smooth motion for said float by evenly distributing said liquid about said float.

3. The invention according to claim 2 wherein a limiting spring is included within and positioned by said float chamber outer shell for downwardly biasing said float.

4. The invention according to claim 2 wherein said float chamber outer shell is transparent and said sump means includes a top cover and a sump inlet tube extending downwardly into said sump means to a first point low enough to reach said liquid in said sump means and an air inlet tube spaced from said top cover sufficiently to avoid wetting thereof upon inversion of said sump means and connected to said second fluid passage extending upwardly to a second point higher than said first point to contact the air above said liquid.

5. The invention according to claim 1 wherein said float chamber means includes a transparent float chamber outer shell and said access forming means includes adjacent liquid and air ports providing liquid and air connection between said supply container and said reservoir for automatically filling said reservoir to a predetermined level.

6. The invention according to claim 1 wherein said float chamber means includes a float, a float chamber outer shell defining a float chamber, and a float chamber inlet means, and said movable support means includes a pawl mechanism and a flow indicating scale attached to said sump means, said float chamber outer shell being attached to said pawl mechanism and said flow indicating scale defining ratchet means for selectively engaging said pawl mechanism and said float chamber inlet means being for depositing liquid into said float chamber.

7. The invention according to claim 6 wherein said float chamber inlet means are included with said float chamber in sufficient proximity to said float such that liquid flowing through said float chamber inlet means does not form drops.

8. An administration set for the infusion of a supply liquid in a supply container into a separate liquid system comprising means for forming an access for liquid flow from the container, sump means for providing an intermediate reservoir and flow of liquid, float chamber means for controlling liquid flow from said sump means, metering flow means for providing a conduit for said liquid from said sump means to said float chamber means and movable support means for said float chamber means for maintaining a substantially constant head of fluid between said sump means and said float chamber means, infusion tubing for conducting liquid from said float chamber means to said separate liquid system, said metering flow means including first and second fluid passages for liquid and air flow to eliminate substantial pressure differentials between said sump means and said float chamber means, whereby as said supply container empties, the flow rate through said metering flow means remains substantially constant, said sump means comprising a drip nozzle leading from said supply container, a reservoir portion, an over-flow portion, a dam means separating said portions and for maintaining a predetermined level of liquid in said reservoir portion, said dam means including an air inlet tube leading to said metering flow means and liquid inlet means for enabling flow of liquid in said reservoir portion to said metering flow means and said drip nozzle being adapted and arranged to supply liquid to said reservoir portion.

9. The invention according to claim 8 wherein said sump means includes an outer sump shell which is transparent for at least part of its surface area enabling observation of the liquid supply from said drip nozzle.

10. An administration set for the infusion of a supply liquid in a supply container into a separate liquid system comprising means for forming an access for liquid flow from the container, sump means for providing an intermediate reservoir and flow of liquid, float chamber means for controlling liquid flow from said sump means, metering flow means for providing a conduit for said liquid from said sump means to said float chamber means and movable support means for said float chamber means for maintaining a substantially constant head of fluid between said sump means and said float chamber means, infusion tubing for conducting liquid from said float chamber means to said separate liquid system, said metering flow means including first and second fluid passages for liquid and air flow to eliminate substantial pressure differentials between said sump means and said float chamber means, whereby as said supply container empties, the flow rate through said metering flow means remains substantially constant, said float chamber means including a float and a float chamber outer shell, a chamber defined by said float chamber outer shell for containing liquid to buoy said float, a float valve stem projecting downwardly from said float, said float chamber outer shell defining a valve seat opening constructed to receive said stem and one of said float chamber shell and float including a plurality of centering splines for centering said float, said float chamber outer shell being attached to a pawl mechanism, a flow indicating scale being attached to said sump means, said flow indicating scale defining ratchet means for selectively engaging said pawl mechanism and float chamber inlet means being included with said float chamber means to deposit liquid into said float chamber.

11. The invention according to claim 10 wherein said float chamber inlet means is a vented nozzle connected to said metering flow means and defining a vent hole to the chamber defined by said float chamber outer shell, said vented nozzle including an exit port located sufficiently below said vent hole so that back pressure level variations are not transmitted to the metering flow means and whose exit port is sufficiently separated from said float so that drops of liquid are formed to drop onto said float.

* * * * *